(12) United States Patent
Berghash et al.

(10) Patent No.: US 6,499,494 B2
(45) Date of Patent: Dec. 31, 2002

(54) DENTURE CLEANER

(76) Inventors: Robert D. Berghash, 73 Oakgrove Dr., Cheektowaga, NY (US) 14221; Merry Riehm-Constantino, 625 Lafayette Ave., Buffalo, NY (US) 14222

( * ) Notice: Subject to any disclaimer, the term of this patent is extended or adjusted under 35 U.S.C. 154(b) by 0 days.

(21) Appl. No.: 09/745,592

(22) Filed: Dec. 26, 2000

(65) Prior Publication Data

US 2002/0078981 A1 Jun. 27, 2002

(51) Int. Cl.$^7$ ................................................ B08B 3/04
(52) U.S. Cl. ........................ 134/135; 134/201; 134/200
(58) Field of Search ............................. 134/117, 135, 134/201, 82, 200, 92

(56) References Cited

U.S. PATENT DOCUMENTS

| | | | | |
|---|---|---|---|---|
| 419,497 A | * | 1/1890 | Caradine |
| 524,621 A | * | 8/1894 | Tinklepaugh |
| 528,875 A | * | 11/1894 | Harrison |
| 536,889 A | * | 4/1895 | Nolen, Jr. |
| 556,358 A | * | 3/1896 | Maxfield |
| 607,134 A | * | 7/1898 | Rightmire |
| 1,187,498 A | * | 6/1916 | Castle |
| 1,597,132 A | * | 8/1926 | Wheelock |
| 1,664,921 A | * | 4/1928 | Goldman |
| 2,156,464 A | * | 4/1939 | Anschicks |
| 2,163,862 A | * | 6/1939 | Wing |
| 2,318,842 A | * | 5/1943 | Eaton |
| 2,443,988 A | * | 6/1948 | Morse |
| 2,541,595 A | * | 2/1951 | Marshall |
| 2,669,243 A | * | 2/1954 | Reynolds et al. |
| 2,675,012 A | * | 4/1954 | Scales |
| 2,806,123 A | * | 9/1957 | Steinbock, Jr. |
| 3,009,468 A | * | 11/1961 | Eberle |
| 3,098,496 A | * | 7/1963 | Milborne |
| 3,121,438 A | * | 2/1964 | Kennedy |
| 3,404,695 A | * | 10/1968 | Paul |
| 3,421,528 A | * | 1/1969 | Gomez et al. |
| 3,732,973 A | * | 5/1973 | Crawford |
| 3,894,551 A | * | 7/1975 | Stohlman |
| 3,904,058 A | * | 9/1975 | Rosenstein |
| 3,966,408 A | * | 6/1976 | Drennen et al. |
| 4,054,220 A | * | 10/1977 | Rosenstein |
| 4,724,855 A | * | 2/1988 | Jackson et al. |
| 4,732,187 A | * | 3/1988 | Monch |
| 4,891,857 A | * | 1/1990 | Pinsonneault |
| 4,922,939 A | * | 5/1990 | Adamczyk |
| 5,000,209 A | * | 3/1991 | Mann |
| 5,184,718 A | * | 2/1993 | Albert |
| 5,275,185 A | * | 1/1994 | Florjancic |
| 5,402,810 A | * | 4/1995 | Donley |
| 5,515,877 A | * | 5/1996 | Dunn, Jr. |
| 5,758,675 A | * | 6/1998 | Scheyer |
| 5,906,216 A | * | 5/1999 | Barlet |
| 5,988,190 A | * | 11/1999 | Borges |
| 6,217,933 B1 | * | 4/2001 | Edwards et al. |

FOREIGN PATENT DOCUMENTS

| | | | |
|---|---|---|---|
| FR | 994495 | * | 8/1951 |
| FR | 2738479 | * | 3/1997 |
| FR | 2760350 | * | 9/1998 |
| GB | 13063 | * | of 1897 |
| JP | 10-244233 | * | 9/1998 |
| JP | 11-151256 | * | 6/1999 |

OTHER PUBLICATIONS

European Patent Application (EPO) 465,285 Jan. 1992.*

* cited by examiner

Primary Examiner—Frankie L. Stinson

(57) ABSTRACT

A device (20) for cleaning dentures broadly includes a cup (21) adapted to hold a liquid (L), and a strainer (29) associated with the cup. The cup as an upper peripheral lip (24). The strainer (29) is a basket-like member having a foraminous bottom (30). The strainer is adapted to be lowered into the cup to submerge a denture contained within the strainer in the liquid. The strainer has at least one hook (35) that is adapted to selectively engage the cup lip (24) such that the strainer may be held in an elevated position relative to the cup such that liquid on the denture may drain into the cup.

5 Claims, 2 Drawing Sheets

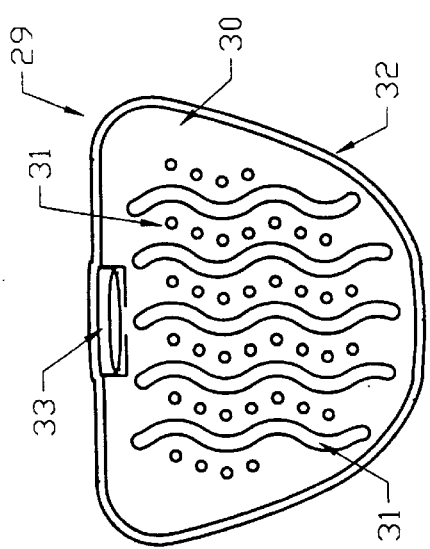
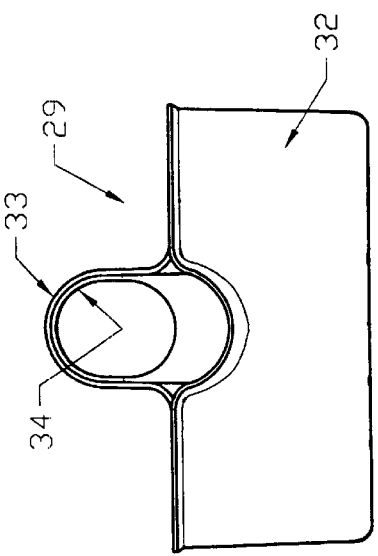
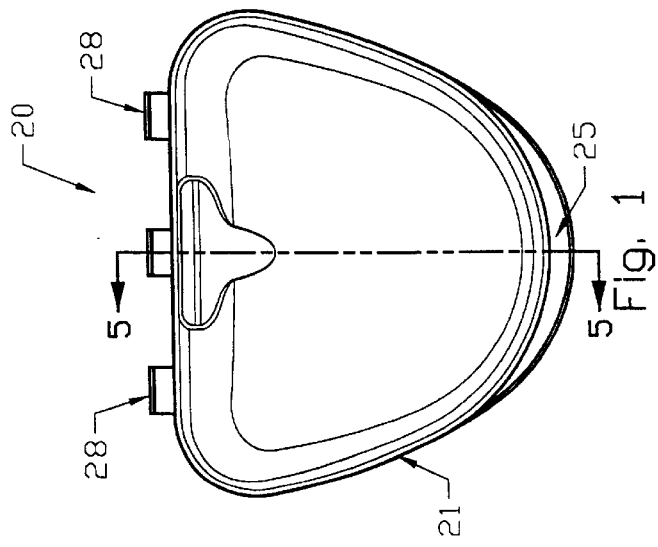
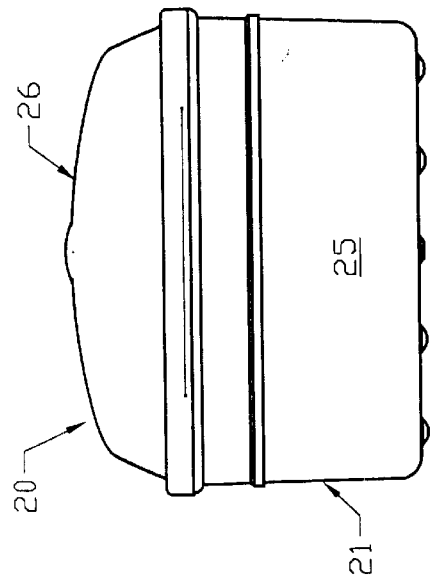

DENTURE CLEANER

TECHNICAL FIELD

The present invention relates generally to devices for cleaning dentures, and, more particularly, to an improved device in which a strainer is operatively arranged within a cup. The strainer is adapted to be moved between a lowered position at which a denture may be submerged in a liquid contained within the cup, and a raised position in which the strainer may be held on the cup in a overhead position such that liquid may drain from the strainer back into the cup.

BACKGROUND ART

Dentures are a boon for some and a bane for others. In any event, they must be cleaned periodically. It is known to submerge a denture in a liquid, and to thereafter soak the denture in the liquid for a predetermined period of time. However, when the denture is removed from the liquid, it would be generally desirable to drain excess liquid from the denture. At the same time, it would be desirable to avoid having to reach into the liquid to physically grasp the denture.

DISCLOSURE OF THE INVENTION

With parenthetical reference to the corresponding parts, portions or surfaces of the disclosed embodiment, merely for purposes of illustration and not by way of limitation, the present invention broadly provides an improved device (20) for cleaning dentures.

In one aspect, the improved device broadly includes a cup (21) adapted to hold a liquid (L) and having an upper peripheral lip (24); and a strainer (29) operatively associated with the cup. The strainer has a foraminous bottom (30) and is adapted to be lowered into the cup to submerge a denture (D) contained within in the strainer in the liquid (see FIG. 5). The strainer has at least one hook (35) adapted to selectively engage the lip of the cup such that the strainer may be held in an elevated position relative to the cup such that liquid on the denture may drain back into the cup (see FIG. 6). The strainer may also have an eye (34) to facilitate passage of a person's finger (not shown) such that the user will not have to reach into the liquid to grasp his dentures.

In the preferred embodiment, the cup and strainer have interfitting generally-polygonal profiles. A lid (26) may be pivotally mounted on the cup, and may be selectively movable between an open position (see FIG. 6) at which a person may have access to the strainer, and a closed position (see FIG. 5). The lid may be connected to the cup by means of at least one living hinge (28). The eye comprises a lifting member (33) mounted on the strainer to facilitate a person in grasping the strainer.

In another aspect, the improved device (20) broadly comprises a cup (21) adapted to hold a liquid (L) and having an upper peripheral lip (24); and a strainer (29) operatively associated with the cup. The strainer again has a foraminous bottom (30). The strainer is adapted to be lowered into the cup to submerge a denture contained therein in the liquid (see FIG. 5), and is adapted to be held in an elevated position relative to the cup such that liquid on the denture may drain back into the cup (see FIG. 6). The strainer may have a lifting member (33) to facilitate a person in grasping the strainer.

Accordingly, the general object of the invention is to provide an improved device for cleaning dentures.

Another object is to provide an improved device for cleaning devices having a cup and strainer, wherein the strainer is adapted to be releasably held in an elevated overhead position such that excess liquid on the denture may drain back into the cup.

Still another object is to provide an improved device for cleaning dentures having a cup and strainer, and with means for facilitating a person's grasp on the strainer such that the user does not have to stick his fingers into the denture cleaning liquid.

These and other objects and advantages will become apparent from the foregoing and ongoing written specification, the drawings and the appended claims.

DESCRIPTION OF THE DRAWINGS

FIG. 1 is a top plan view of the improved device, with the lid shown as being in its closed position.

FIG. 2 is a front elevation of the device shown in FIG. 1.

FIG. 3 is a top plan view of the strainer.

FIG. 4 is a front elevation of the strainer shown in FIG. 3.

DESCRIPTION OF THE PREFERRED EMBODIMENTS(S)

Figure 6:
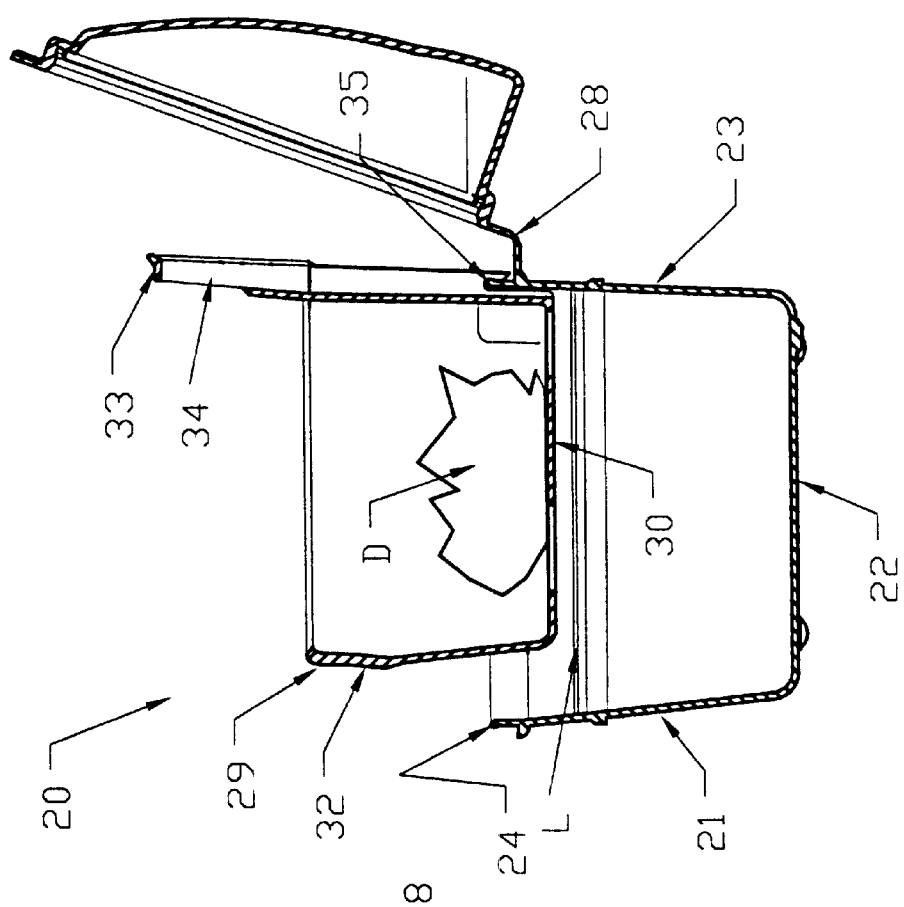
FIG. 6 is a view generally similar to FIG. 5, but showing the lid as having been opened, and further showing the strainer as being held in its elevated position relative to the cup, such that liquid may drain back into the cup.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Figure 5:
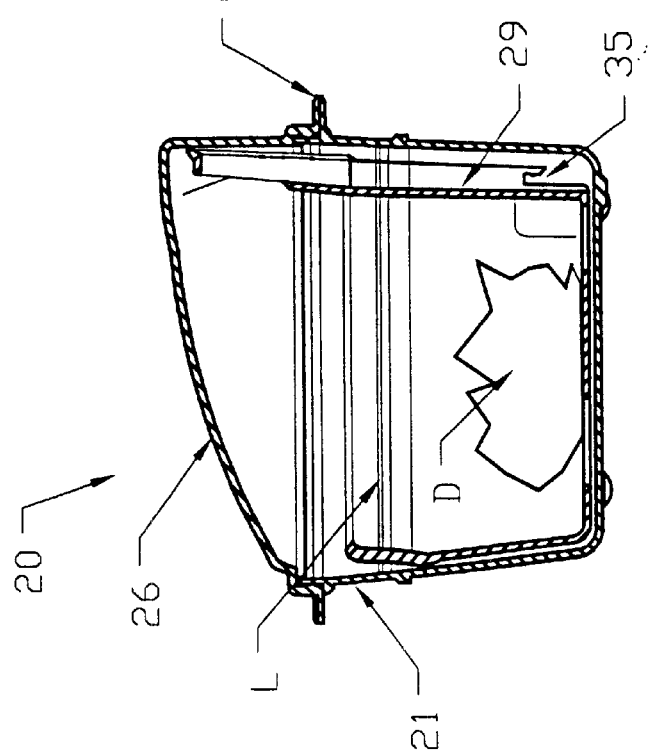
FIG. 5 is a fragmentary vertical sectional view thereof, taken generally on line 5—5 of FIG. 1, showing the strainer as being in its lowered position within the cup.

Referring now to the drawings, and, more particularly to FIGS. 1–2 and 5–6 thereof, the present invention provides an improved device, generally indicated at 20, for cleaning dentures. In FIGS. 5 and 6, the dentures are graphically illustrated as being an object D.

The improved device is shown as broadly including a cup, generally indicated at 21, that is adapted to hold a liquid. In FIGS. 5 and 6, the liquid level is indicated as being L. The cup is shown as being a somewhat polygonal member, when seen in top plan. When seen in transverse cross-section, the cup is shown as having a planar horizontal bottom portion 22, and is provided with a generally upstanding peripheral wall 23 terminating in an uppermost peripheral lip 24. As noted above, when seen in top plan, the cup has a generally triangular shape, with a rounded forward edge, indicated at 25 in FIG. 1. A cover, generally at indicated at 26, is joined to the cup by means of three horizontally-spaced living hinges, severally indicated at 28. The cover has an appropriate recess into which the upper peripheral lip of the cup may be received to cause the cover to snap into engagement with the lip. This provides a substantially liquid-tight seal when the cover is closed.

The device is shown as further including a basket-like strainer, generally indicated at 29. As best shown in FIG. 3, the strainer has a planar horizontal bottom 30 provided with a plurality of holes, severally indicated at 31. Thus, the bottom of the strainer basket is foraminous. The strainer also has a peripheral side wall 32 which generally simulates the polygonal outline or profile of the cup. A member 33 rises upwardly from the rear of the strainer. Member 33 has a hole 34 which is adapted to receive insertion of a person's finger. Thus, a user may insert his finger through hole 34 to facilitate his grasp on the strainer basket.

As shown in FIG. 5, te strainer is adapted to be lowered into the cup to submerge a denture contained within the strainer in the liquid. However, the strainer has at least one hook, generally indicated at 35. As best shown in FIG. 6, hook 35 is arranged to selectively engage the peripheral cup lip 24 such that the strainer basket may be held in an elevated position relative to the cup such that liquid on the denture may drain back into the cup. There may be one hook, or a plurality of hooks, depending on the particular design. Thus, the basket is associated with the cup for selective movement between a lowered position at which the strainer basket simply rests on the bottom of the cup, with an object contained in the strainer basket being submerged in the liquid, and an alternative raised or elevated position, such as shown in FIG. 6, to allow liquid within the strainer basket and on the object to drain down through the foraminous bottom of the strainer basket into the cup.

Modifications

The present invention contemplates that many changes and modifications may be made. For example, the shape and configuration of the cup member may be changed or varied, as desired. While the preferred form is shown as having a complementarity-configured strainer that fits within the profile of the cup in only one relative angular position therebetween, this need not invariably obtain. For example, in an alternative design, the cup might be polygonal profile, and the strainer might have a polygonal outline, or vice versa. Similarly, while it is desired that the device have a cover or lid, and preferably one that lockingly interfits with the cup, this is not invariable. Such a cover might be completely detachable from the cup. Indeed, the cover might possibly be omitted altogether. Thus, the living hinge, disclosed in the preferred embodiment, is only one specific form of the invention. Similarly, while the preferred embodiment is shown as having an eye to facilitate a person's grasp on the strainer, this structure may readily be changed. For example, a tab, or some other means or mechanism to facilitate a person's grasp might alternatively be used. The materials of construction are not deemed to be particularly critical, and may readily be changed or desired. In the preferred embodiment, a suitable flavorant is molded integrally with the cup to increase the aromatic appeal of the device.

Therefore, while the presently preferred form of the improved device as been shown and described, and several modifications thereof discussed, persons skilled in this art will readily appreciate that various additional changes and modifications may be made without departing from the spirit of the invention, as defined and differentiated by the following claims.

What is claimed is:

1. A device for cleaning dentures, comprising:

a cup adapted to hold a denture cleaning liquid, said cup having an upper peripheral lip;

a strainer shaped to receive a denture and operatively associated with said cup, said strainer having a foraminous bottom and being adapted to be lowered into said cup to submerge the denture in said strainer in the liquid, and said strainer having at least one hook formed integrally with said strainer and adapted to selectively engage said cup lip such that said strainer may be held by said hook in an elevated position relative to said cup such that liquid on the denture may drain into said cup; and a lid pivotally mounted on said cup by a living hinge, said lid being selectively movable between an open position at which a person may have access to said strainer and a closed position, wherein said cup and said strainer have interfitting polygonal profiles.

2. A device for cleaning dentures as set forth in claim 1 and further comprising a lifting member mounted on said strainer for lifting said strainer, said lifting member comprising an eye.

3. A device for cleaning dentures as set forth in claim 2 wherein said eye extends upwardly from said strainer.

4. A device for cleaning dentures, comprising:

a cup adapted to hold a denture cleaning liquid, said cup having an upper peripheral lip;

a strainer shaped to receive a denture and operatively associated with said cup, said strainer having a foraminous bottom, said strainer being adapted to be lowered into said cup to submerge a denture in said strainer in the liquid and adapted to be held in an elevated position relative to said cup such that liquid on the denture may drain into said cup, and wherein said strainer has a lifting member for lifting said strainer, said lifting member comprising an eye; and a lid pivotally mounted on said cup by a living hinge, said lid being selectively movable between an open position at which a person may have access to said strainer and a closed position, wherein said cup and said strainer have interfitting polygonal profiles.

5. A device for cleaning dentures as set forth in claim 4 wherein said eye extends upwardly from said strainer.

\* \* \* \* \*